United States Patent [19]

Wang

[11] Patent Number: 5,205,278
[45] Date of Patent: Apr. 27, 1993

[54] CHEMICAL BAG WARMER

[76] Inventor: Ching-Chuan Wang, No. 17. Lane 16. Ying-An street, Yung-Ho, Taipei, Taiwan

[21] Appl. No.: 877,834

[22] Filed: May 1, 1992

[51] Int. Cl.$^5$ ............................................. F24J 1/00
[52] U.S. Cl. .................................. 126/263; 422/245; 126/204; 128/403
[58] Field of Search ............... 126/263, 204, 205, 206; 165/10 A; 604/289-291; 128/399-403; 62/259.3; 422/245, 246

[56] References Cited

U.S. PATENT DOCUMENTS

| | | | |
|---|---|---|---|
| 4,460,546 | 7/1984 | Kapralis et al. | 126/263 X |
| 4,532,110 | 7/1985 | Kapralis et al. | 126/263 X |
| 4,572,158 | 2/1986 | Fiedler | 126/263 |
| 5,058,563 | 10/1991 | Manker | 126/263 |

Primary Examiner—Larry Jones
Attorney, Agent, or Firm—W. Wayne Liauh

[57] ABSTRACT

An improvement of a chemical bag warmer, which comprises a soft bag filled with a sodium acetate solution, and mounted therein with a triggering member; the triggering member is a disc-shaped member, of which the center portion is a cross-shaped part extended to the edge thereof to divide the center portion into four sectors; each sector has a plurality of fragmental concentric circles to form into a rugged surface, the rugged surface can facilitate the triggering member to bend and vibrate so as to generate a better oscillation wave effect.

2 Claims, 1 Drawing Sheet

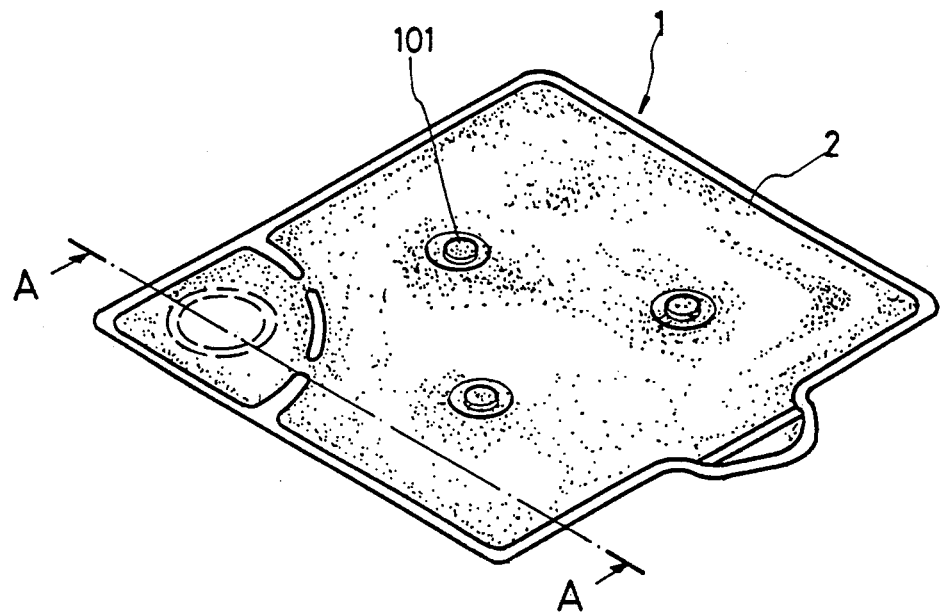
F I G. 1
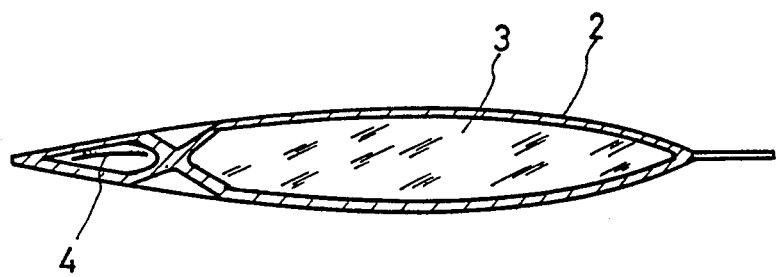
F I G. 2 (A-A)
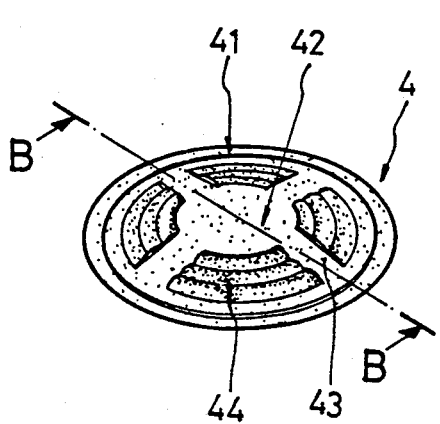
F I G. 3
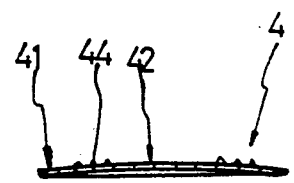
F I G. 4 (B-B)

CHEMICAL BAG WARMER

BACKGROUND OF THE INVENTION

Currently, there are many kinds of warm-producing apparatuses or warmers in the market, and the theory of producing a warm effect thereof is also different from one another; for instomce, a pocket warmer in the portable warmer category uses battery to generate a warm temperature; such a warmer has drawbacks of having more weight and replacing battery quite often aside from the inconvenience in use and high price. A conventional warmer uses coal as a means to generate heat; apparently, it is deemed a hazardous warmer to the user because of being easily to cause a fire or to burn the user aside from the inconvenience.

There is a warmer, of which the heat is generated with a hot water filled therein; unfortunately, it has a drawback of large size to cause inconvenience upon carrying around; it can only be used within a limited area. There is another type of warmer, of which the heat is generated with electric power, but it can only be used indoors.

Later on, there was a chemical bag warmer developed; such a bag comprises a sodium acetate solution and a triggering member made of a metal piece. When triggering member is operated, an oscillation wave will be generated to cause the sodium acetate solution to generate a crystallization heat as a warming means. Such a chemical bag warmer has the advantages of portability, low price, and better warming effect; therefore, it has become a popular warmer in the public.

Prior art devices were described as early as 1978 such as in U.S. Pat. No. 4,077,390, which describes a flexible container filled with a super-cooled aqueous salt solution and also containing a flexible ferrous metal strip characterized by one or more fissures or slits which are said to initiate crystallization of the solution when the metal strip is flexed. The fissure or slit is so prepared that the opposing sides of the fissure do not touch or scrape one another but ultimately taper to and terminate in a blind end.

Heat packs made in accordance with the teachings of U.S. Pat. No. 4,077,390 prove to have serious drawbacks in practical use. The continual bending to initiate crystallization can create a break in the activator strip along the lines of the slits or cuts. Once broken the effectiveness is lost and the heat pack becomes unusable. Furthermore, the broken metal can cause a puncture in the heat pack and undesirable leakage of the salt solution.

U.S. Pat. No. 4,379,448 recognized the shortcomings of the aforesaid heat pack and attempted to modify the problem by placing slits on the inside of the trigger with none of them extending to the marginal edges of the strip. Further, the patentee employs the concept of a snap-displacement of the metal, the so-called "oil can" effect when the metal is subjected to flexing or bending. Once again the heat pack failed to perform with sufficient reliability in actual use since there was a percentage of the units which failed to activate despite any amount of flexing of the metal part. The same patentee tried an alternative construction in U.S. Pat. No. 4,460,546 wherein he introduced pinhole openings in the metal strip in place of the fissures or slits shown in his previous patent. This patentee introduced a non ferrous metallic strip of a Berylium-copper alloy or phosphor bronze, in order to avoid the deficiencies of the stainless steel trigger employed in earlier constructions. Heat packs made in this way likewise still were not completely satisfacotry. The "oil can" effect can result in snap-deflection accidentally instances no amount of bending or snap action can cause the activation of the contents of the heat pack.

Still another attempt was made in U.S. Pat. No. 4,572,158 to resoive the problem of failures by making A least one major cut extending completely through the metal part and positioned totally within the exterior perimeter thereof. and making the slit wide enough so that the opposed facing deges are always spaced one from the other. Then the patentee made a second minor slit at one end or the other of the major slit and at an angle to the major slit. Again the minor slit is formed with two opposing facing edges that are minutely spaced one from the other so that they do not touch during manipulation. This patent also employed the snap displacement or "oil-can" effect. Flexible plastic heat packs of the type referred to above are shown in such U.S. patents as U.S. Pat. Nos. 4,379,448 and 4,460,546. The heat pack shown in these patents are unsatisfactory for microwave regeneration because such packs are known to contain internal welds which cause confined spaces within the pack resulting in hot spotting and melting or weakening of the flexible plastic pouch which thereby renders the heat pack unusable. In fact, such heat packs actually have carried a warning notice that the contents should not be microwaved to recharge or regenerate them.

U.S. Pat. No. 4,872,442 disclosed a highly reliable activator which is provided for initiating the crystallization or destabilization of a super-cooled aqueous salt solution to cause generation of heat in a heat pack. The activator is characterized by a plurality of slits in a flexible metal article, with the opposing sides of the slits being in contact along at least a part of the length of the slit, and by an eroded and roughened surface on said article which comprises a number of minute metal nodules attached to and protruding from the surface, especially at or near the slit, which nodules are adapted to be detached or broken-off upon flexing of the activator. The slits of the flexible metal article comprise a number of minute medal nodules; when the metal nodules are pressed, the slits on the activator will vibrate up and down to generate an oscillation wave. According to the aforesaid invention, the metal nodules is to vibrate up and down for generating an oscillation wave, which can only scatter in two directions (i.e., back and forth). In operation, a user has to apply a stronger force to press and bend the slits so as to have activator vibrating up and down to generate an oscillation wave; such an oscillation would result in an efficiency difference (i.e., being unable to oscillate and scatter in right and left direction); as a result, the heat-generating efficiency thereof is poor, and the heat-generating speed and temperature are limited and low, The U.S. Pat. Nos. 4,880,953 and 4,872,442 were invented by one person, and both patents are deemed tow related inventions. In U.S. Pat. No. 4,872,442, a microwave energy is utilized to thereby melt the solid to the liquid. The method of using microwave energy to generate heat is deemed a well-known means discovered by others long ago. In the aforesaid invention, the heat is to be generated by means of friction between the water molecules, which is deemed a well-known art. Mr Manker uses microwave energy to have a solid in a chemical bag warmer to melt into liquid for generating heat; apparently, it is deemed a well-known art without any novelty.

According to the present invention, heat is to be generated by means of crystallization of a sodium acetate in a bag; the crystallization is obtained by using an oscillation wave. The present invention comprises a soft PVC, P.P. or P.U. bag which can withstand a high temperature and ultraviolet rays, a flexible metal piece as a triggering member to generate an oscillation sound wave, and a sodium acetate solution, of which the molality is ranging from 8 m to 24 m. The prime feature of the present invention is that the triggering member is substantially a disc-shaped flexible metal piece, of which the center portion is a cross-shaped flat part; the cross extends in four directions reaching the edge of the outer circular portion of the triggering member; the center portion is divided into four sectors, of which each has a plurality of fragmental and concentric circles arranged in parallel to form into a rugged surface so as to facilitate the triggering member to be pressed up and down and to generate an oscillation wave in order to cause the bay warmer to generate heat immediately.

Another feature of the present invention is that the triggering member is fixedly installed at one corner of the bag warmer so as to let a user easily control or a blind person easily catch the triggering member to operate the same. The triggering member may also be installed in the bag in a non-fixed manner.

Still another feature of the present invention is that a microwave or other magnetic waves or electric current may be used for re-generating the heat-generating material rapidly.

BRIEF DESCRIPTION OF THE DRAWINGS:

FIG. 1 is a perspective view of an embodiment according to the present invention.

FIG. 2 is a sectional view taken along line A—A in FIG. 1.

FIG. 3 is a perspective view of a triggering member in the present invention.

FIG. 4 is a sectional view taken along line B—B in FIG. 3.

DETAILED DESCRIPTION

Referring to FIGS. 1 and 2, the chemical bag warmer 1 comprises a sealed bag 2 made of PVC, P.P. or P.U. plastics, a sodium acetate solution 3 filled in the sealed bag, and a triggering member 4. The sealed bag 2 is furnished with a plurality of reinforced parts 101 for reinforcing the PVC, P.P. or P.U. bag, and for controlling the solution in an evenly spread manner; otherwise, the solution in the bag would become uneven in the event of being carried by a user to move around.

Referring to FIGS. 3 and 4, the triggering member 4 of the present invention is a disc-shaped member made of a flexible metal, which has an outer circular portion 41, a center portion 42 which is substantially a cross "+" with a flat and smooth surface 43 to divide the center portion 42 into four sectors; the four sectors form into a rugged surface 44 with a plurality of concentric circles. The triggering member 4 according to the present invention is a specially designed one. When the triggering member is bent up and down to vibrate completely, it will generate an oscillation wave to concentrate in the center thereof so as to have a sodium acetate solution 3 in the heating bag reached the maximum reaction effect in the shortest time.

Since the center portion 42 is designed into a cross "+" shape, it can have the vibration easily directed to four directions so as to generate a heat quickly in the bag.

The bag warmer according to the present invention is assembled with a sodium acetate solution and a triggering member 4 to be loaded in the sealed bag 42, in which air is completely exhausted; then, the bag 42 is to be sealed with an ultra-high frequency bonding method. The molality of the sodium acetate solution 3 should be controlled within a range from 8 m to 24 m according to the actual condition required so as to have the sodium acetate solution at room temperature in a fluid state. To operate the bag warmer, a user may simply apply a pressure to the triggering member 4 repeatedly so as to cause the member 4 to generate an oscillation sound wave, which will trigger the sodium acetate solution to have a crystallization reaction continuously until a crystallization heat being released; the heat released can have a temperature ranging from 35° C. to 75° C. for about several minutes to three hours; therefore, the present invention is deemed a practical, convenient, and portable heating bag to keep warm for a given period of time.

After the heat being dissipated completely, the sodium acetate solution will be converted into a solid crystalline state; the solid crystalline sodium acetate can be converted into solium acetate solution simply by placing the bag in a hot water (over 80° C.) for a given period of time, and then the bag warmer can be used again.

I claim:

1. A chemical bag warmer comprising:

a plastic bag sealed completely;

a sodium acetate solution being filled in said sealed bag, said sodium acetate solution having a molality ranging from 8 m to 24 m;

a triggering member disposed in said sodium acetate solution, said triggering member being adapted to generate an oscillation wave when a pressure is applied thereupon causing said triggering member to bend;

said triggering member being a disc-shaped member made of a flexible metal piece, said triggering member being characterized by having a flat outer circular portion, a flat center portion, and a rugged middle portion therebetween, said middle portion comprising a plurality of segmented and rugged concentric annuluses separated by a plurality of channel-shaped flat surfaces extending from said center portion to said outer circular portion;

said triggering member is adapted to vibrate and generate an oscillation wave when a pressure is applied thereupon, thereby causing said sodium acetate solution to crystallize and providing a warming effect through the dissipation of heat due to such crystallization.

2. The chemical bag warmer of claim 1 wherein said channel-shaped flat surfaces have a cross "+" shape.

* * * * *